US006635800B2

United States Patent
Jackson et al.

(10) Patent No.: US 6,635,800 B2
(45) Date of Patent: Oct. 21, 2003

(54) SEGMENTED TAMPON PLEDGET

(75) Inventors: Dane R. Jackson, Bloomingdale, NJ (US); Jacqueline Davis, Revere, MA (US); Rosemary F. Knuth, Congers, NY (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 09/839,061

(22) Filed: Apr. 20, 2001

(65) Prior Publication Data

US 2002/0156442 A1 Oct. 24, 2002

(51) Int. Cl.[7] ............................ A61F 13/15; A61F 13/20
(52) U.S. Cl. .................... 604/378; 604/904; 604/385.18
(58) Field of Search ..................... 604/385.17, 385.18, 604/904, 11–18, 378

(56) References Cited

U.S. PATENT DOCUMENTS

| 2,330,257 A | | 9/1943 | Bailey ........................... 18/55 |
|---|---|---|---|
| 2,858,831 A | * | 11/1958 | Graham ....................... 128/285 |
| 3,371,666 A | * | 3/1968 | Lewing ....................... 128/285 |
| 3,572,341 A | * | 3/1971 | Glassman ................... 128/285 |
| RE27,677 E | | 6/1973 | Glassman ................... 128/270 |
| 3,834,389 A | | 9/1974 | Dulle .......................... 128/285 |
| 3,841,333 A | | 10/1974 | Zalucki ....................... 128/285 |
| 3,965,905 A | | 6/1976 | Schoenholz et al. ........ 128/285 |
| 4,271,835 A | | 6/1981 | Conn et al. .................. 128/270 |
| 4,335,720 A | | 6/1982 | Glassman .................... 128/270 |
| 4,341,214 A | * | 7/1982 | Fries et al. .................. 128/285 |
| 4,553,965 A | | 11/1985 | Conn et al. .................. 604/286 |
| 5,004,467 A | | 4/1991 | Hinzmann et al. .......... 604/904 |
| 5,542,914 A | | 8/1996 | Van Iten ...................... 604/11 |
| 5,584,827 A | * | 12/1996 | Korteweg et al. ........... 604/369 |
| 6,156,021 A | | 12/2000 | Tojkander .............. 604/385.17 |

FOREIGN PATENT DOCUMENTS

WO    WO 00/61052    10/2000

* cited by examiner

Primary Examiner—Weilun Lo
Assistant Examiner—C. Lynne Anderson
(74) Attorney, Agent, or Firm—Ohlandt, Greeley. Ruggiero & Perle, LLP

(57) ABSTRACT

There is provided a tampon having a plurality of pledget segments with each segment having one or more layers of absorbent material and one or more layers of semipermeable material. The one or more semipermeable layers of each segment forms an absorption restriction boundary to the next adjacent segment that allows each segment to absorb and expand independently from the other segments. The plurality of pledget segments can be positioned in a coverstock bag.

36 Claims, 2 Drawing Sheets

SEGMENTED TAMPON PLEDGET

BACKGROUND OF THE INVENTION

1. Field of the Invention

The present invention relates to a tampon and, in particular, to a tampon having a plurality of segments of absorbent material.

2. Description of the Prior Art

Tampons constructed of a plurality of segments of absorbent material are known. For example, tampons having a plurality of absorbent layers spaced along a thread are described in U.S. Pat. Nos. 3,965,905 and 5,542,914 as having increased absorption capacity due to increased surface area. U.S. Pat. No. 3,965,905 describes the spacing between adjacent absorbent layers to be such that they do not contact one another so as to enhance expansion of the segmented tampon into irregular shapes. The individual segments of the tampons shown in these patents bloom (expand when saturated with fluid) substantially together.

U.S. Patent Re. 27,677 discloses a tampon having an interior layer and an exterior layer of absorbent material with an intermediate layer of moisture impervious material that has an array of perforations. The perforations are described as directing rapid and/or initial flow of menstrual fluid to the interior layer. However, the perforations, being located between the two layers, will allow fluid to flow to each of the layers simultaneously. The net result is that the interior and exterior layers bloom substantially together.

U.S. Pat. No. 4,335,720 discloses a tampon that prevents strikeover or premature swelling of the insert end of the tampon that causes fluid flow along the outside thereof. The tampon is formed of an interior layer and an exterior layer of absorbent material separated by a layer of impervious material. A hollow core with radial slots is formed within the interior layer. Both the hollow core and the radial slots open to the insertion end of the tampon. Fluid at the insertion end is directed by way of the open end of the core and the radial slots to the interior core for absorption by the interior layer. This tends to retard strikeover or premature swelling of the insert end.

SUMMARY OF THE INVENTION

It is an object of the present invention to provide a tampon that has a plurality of pledget segments that absorb and expand independent of one another.

It is another object of the present invention to provide such a tampon that has a plurality of pledget segments with each segment having motion flexibility that is independent of an adjacent segment, thereby providing user comfort.

It is still another object of the present invention to provide such a tampon where the plurality of pledget segments are contained in a coverstock bag, thereby providing enhanced user comfort.

It is a further object of the present invention to provide such a tampon where the semipermeable layer of the segment at the insertion end of the tampon is extended to surround the plurality of pledget segments and form a cover.

It is still a further object of the present invention to provide such a tampon where the pledget segment at the insertion end of the tampon is fixed to a withdrawal cord, while the remaining plurality of pledget segments are not fixed to the withdrawal cord and are able to float along the cord.

These and other objects of the present invention are achieved by a tampon that has a plurality of segments positioned along an axis, such as, a withdrawal cord, so as to permit expansion movement of any segment during absorption independent of other segments. Each of the segments includes one or more absorbent layers and one or more layers of semipermeable material that form the bottommost layer of the segment. The bottom, or final segment, at the withdrawal end of the pledget, may not have the semipermeable material. The layers of semipermeable material act as absorption barriers that delay substantial fluid absorption by the absorbent layers of a next segment until the absorbent layers of a preceding segment have absorbed fluid and expanded substantially. This allows each segment to absorb and expand independently from the other segments.

To further enhance user comfort, the plurality of pledget segments may be contained in a coverstock bag that either totally encases the pledget segments or a coverstock that is open at the insertion end of the tampon.

BRIEF DESCRIPTION OF THE DRAWINGS

Other and further objects, advantages and features of the present invention will be understood by reference to the following specification in conjunction with the accompanying drawings, in which like reference characters denote like elements of structure and.

DESCRIPTION OF THE INVENTION

Figure 1:
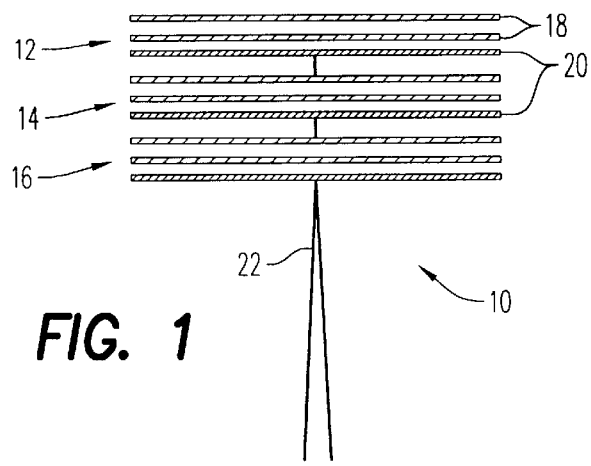
FIG. 1 is an elevation view of a segmented tampon of the present invention prior to compression and heat setting.

Referring to the drawings and, in particular, FIG. 1, there is provided a tampon generally represented by reference numeral 10. Tampon 10 includes a plurality of pledget segments 12, 14 and 16. Each segment 12, 14 and 16 has at least one layer of absorbent material and one layer of moisture semipermeable material separating it from the next segment. For example, pledget segment 12 includes two layers 18 of absorbent material and a layer 20 of moisture semipermeable material.

While the present invention is shown in FIG. 1 as having a number of layers of material, it should be understood that each segment may have any number of groups of the combinations of one or more layers of absorbent material and one or more layers of moisture semipermeable material. For example, the pledget segment may have one, two, or more layers of absorbent material and one, two, or more layers of semipermeable material, followed by a second group of one, two, or more layers of absorbent material and one, two, or more layers of moisture semipermeable material.

In one embodiment of the present invention pledget segments 12, 14 and 16 are attached at intervals along a withdrawal cord 22, forming a stack of segments. The interval lengths are selected to allow absorption, expansion and motion of each pledget segment independent of the other pledget segments. Each layer 20 does not restrict motion of a segment as it expands. Without layers 20, the absorbent fibers of layers 18 of adjacent segments will tend to interlock, thereby restricting motion and absorption of individual segments.

In another embodiment of the present invention, pledget segment 12 is attached and fixed to withdrawal cord 22 to secure all of the segments during removal from the vagina. Pledget segments 14 and 16 are not fixed to a specific location on the withdrawal cord 22 and are able to float, for example approximately 0.5 inches, in either an insertion direction or a removal direction along the cord. The ability of the segments to float along the cord provides increased comfort to the user and further enhances the ability of each segment to absorb fluids and expand independently of one another.

Figure 2:
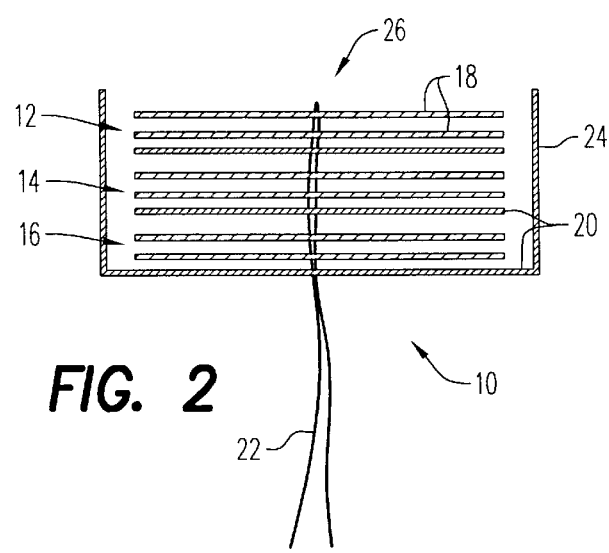
FIG. 2 is an elevation view of a segmented tampon of the present invention having a cover.

Referring to FIG. 2, the tampon pledget segments 12, 14 and 16 are provided with a cover 24 that is formed by extending semipermeable layer 20 of segment 16 to surround all of the segments. While cover 24 is depicted as being open at the insertion end 26, the cover can be formed such that it encases the entire pledget. The extended semipermeable layer 20 can be the same material as the other semipermeable layers 20 or it can be selected from other commercially available coverstocks, such as, for example, a surfactant treated olefin spunbond nonwoven. The extended cover improves pledget removal comfort when the pledget is not fully saturated.

Figure 3:
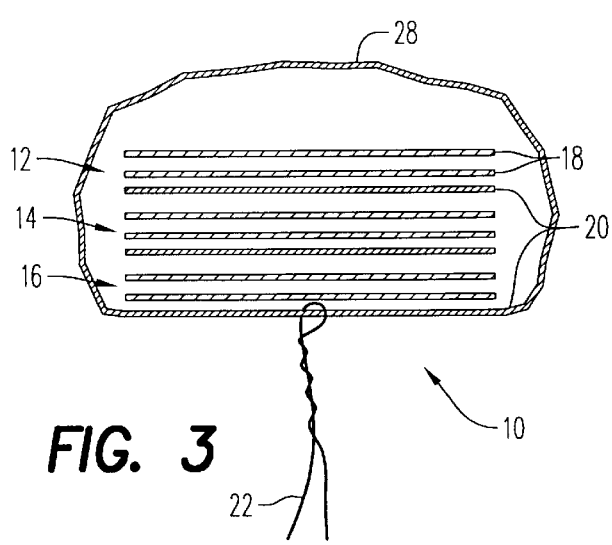
FIG. 3 is an elevation view of another embodiment of a segmented pledget of the present invention having a coverstock bag.

Referring to FIG. 3, the tampon of the present invention is provided with a coverstock bag 28. Pledget segments 12, 14 and 16 are not secured to the withdrawal cord, but are contained in coverstock bag 28. Withdrawal cord 22 is secured to coverstock bag 28 and not segment 12. As a result, all of the segments are free to float within coverstock bag 28 during absorption, but are fully secured within the bag during removal from the vagina. Coverstock bag 28 can be formed from the same semipermeable material used in layers 20, or can be formed from any commercially available coverstock material, such as, for example, surfactant treated olefin spunbond nonwoven coverstock. By encasing the segments within a coverstock, and allowing the segments to float within the coverstock, enhanced absorption and removal comfort is realized.

Figure 4:
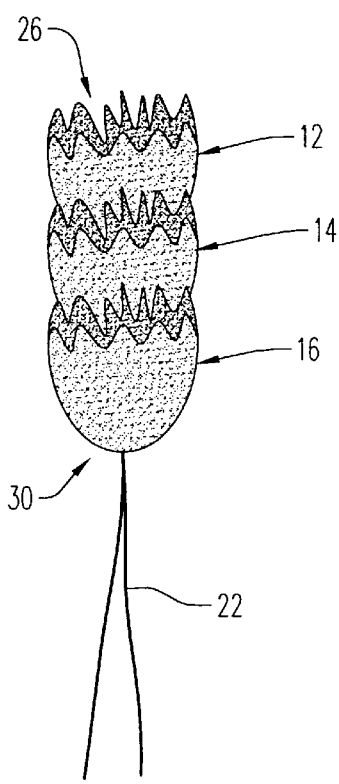
FIG. 4 is an elevation view of a segmented tampon of the present invention after compression and heat setting.

Referring to FIG. 4, pledget segments 12, 14 and 16 are shown as compressed and heat set into cup shapes before encapsulation in an applicator. In this configuration, pledget segment 12 forms an insertion end 26 of tampon 10. Pledget segment 16 forms a withdrawal end 30 of tampon 10.

Referring again to FIG. 1, layer 20 is the bottom-most layer of each pledget segment 12, 14 and 16. The construction is such so as to permit independent fluid absorption by each pledget segment 12, 14 and 16. Thus, pledget segment 12 absorbs fluid independent of the next succeeding pledget segment 14, and bottom-most layer 20 of pledget 12 restricts and delays fluid flow to the next succeeding pledget segment 14. When pledget segment 12 has become saturated with fluid and has expanded, fluid flows through the semipermeable material of its bottom-most layer 20 toward absorbent layers 18 of pledget segment 14.

Pledget segment 14 absorbs fluid independent of the next succeeding pledget segment 16 and its bottom-most layer 20 restricts fluid flow to pledget segment 16. When pledget segment 14 has saturated and expanded, fluid flows through the semipermeable material of its bottom-most layer 20 toward absorbent layers 18 of pledget segment 16. Pledget segment 16 then absorbs fluid. When pledget segment 16 has absorbed and expanded, tampon 10 is fully saturated and spent. Thus, the pledget segments 12, 14 and 16 act as a series of mini pledgets that absorb and expand independently from one another. A result of independent expansion is higher absorption efficiency (grams absorbency/grams fiber) and improved leakage protection. There is also improved user comfort due to the flexibility of the individual segments.

The absorbent material of layers 18 may be any suitable material that is capable of absorbing menstrual fluid, known presently or in the future. For example, the absorbent material may be of a fibrous composition, such as rayon, and preferably rayon with a cross-section modified to a "Y" shape.

The semipermeable material of layer 20 may be any suitable material that restricts and delays the flow of fluid therethrough, known presently or in the future. For example, the semipermeable material may be a coverstock formed from polyethylene/polyester bicomponent fibers that have been thermally fused together to form a consolidated web. This type of coverstock is available from HDK Industries, Inc., and is sold under the codename HDK B1014.

Layers 18 and 20 may have any suitable shape, such as circular, square, ovoid, rectangular, hexagonal, parallelogram, polygonal, and any combination thereof. Preferably, the shape of layers 18 and 20 are circular or hexagonal. The shapes and/or dimensions of layers 18 or 20 can be uniform or non-uniform for the segments. Within a single segment, the dimensions and/or shape layers 18 or 20 can be uniform or non-uniform. The dimensions of a layer are selected to yield an area of a single surface thereof that is preferably in the range of about 0.8 square inches ($in^2$) to about 6.0 $in^2$ and a layer weight that is preferably in the range of about 0.1 grams to about 1.5 grams. In one embodiment of the present invention, layers 18 and 20 are of uniform shape and have a single surface area about 2.65 $in^2$ and single weight of about 0.4 grams. The weights and surface areas can be modified depending on the type and/or blend of the absorbent fibers used and the total number of segments desired.

Although three segments 12, 14 and 16 are shown in FIGS. 1 through 4, it will be apparent to those skilled in the art that the number of segments can be any number greater than one.

The interval lengths between adjacent pledget segments 12, 14 and 16 are preferably in a range that is less than the maximum dimension of either layer 18 or 20. In preferred designs, the maximum dimension of each layer 18 is on the order about 1 to about 2 inches and the interval length is preferably in the range of about 0.1 inch to about 1.5 inches. More preferably, the interval range is about 0.125 inch to about 1 inch. Most preferably, the interval range is about 0.25 to about 0.5 inch. In one embodiment, the interval length is about 0.25 inch.

Figure 5:
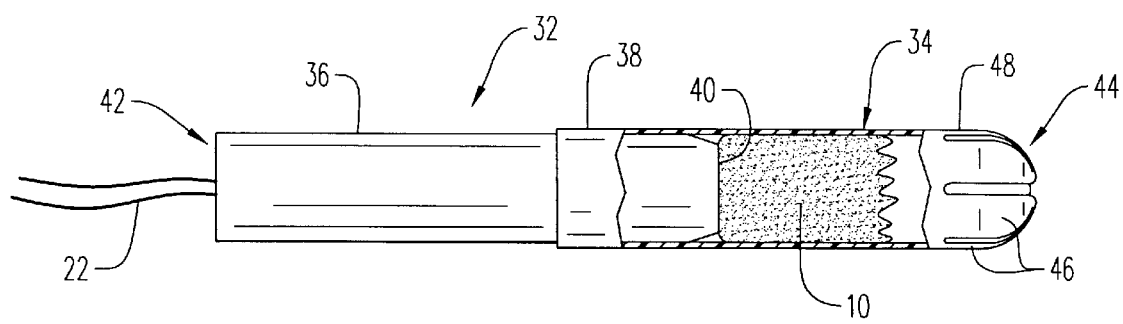
FIG. 5 is a side view of an applicator for the segmented pledget of the present invention.

Referring to FIG. 5, an applicator 32 has a barrel 34 and a plunger 36 telescopically in a rear portion 38 of barrel 34. After compression and heat setting, tampon 10 is positioned in the forward end of barrel 34 and is abutted by a forward end 40 of plunger 36. Withdrawal cord 22 extends outwardly through rear end 42 of plunger 36. Barrel 34 preferably includes a dome shaped front end 44. Preferably, the front end 44 has a plurality of petals 46, and these petals are preferably inwardly folded about a base region 48. When plunger 36 is moved forward, its forward end 40 pushes tampon 10 toward and out front end 44 of barrel 34. Petals 46 are forced to bend outwardly as tampon 10 is ejected. After ejection, the petals 46 substantially return to their original position for comfortable removal of applicator 32.

It will be apparent to those skilled in the art that applicator 32 is one example of an applicator that may be used with tampon 10. Alternatively, the tampon may be inserted into the vagina without the aid of an applicator simply by guiding it with a user's finger.

The present invention having been thus described with particular reference to the preferred forms thereof, it will be obvious that various changes and modifications may be made therein without departing from the spirit and scope of the present invention as defined in the appended claims.

What is claimed is:

1. A tampon comprising:
a plurality of segments positioned at unoccupied intervals along an axis, each of said plurality of segments having an absorbent layer and a layer of semipermeable material, and
wherein said layer of semipermeable material acts as an absorption barrier that restricts and delays substantial fluid absorption by the absorbent layer of a next one of said plurality of segments until said absorbent layer of a preceding one of said plurality of segments has substantially absorbed and expanded.

2. The tampon of claim 1, wherein at least one of said plurality of segments includes two or more adjacent absorbent layers.

3. The tampon of claim 2, wherein each of said plurality of segments includes two or more adjacent absorbent layers.

4. The tampon of claim 1, wherein said intervals is at least one interval.

5. The tampon of claim 4, wherein said at least one interval has a length that is in the range about 0.1 inch to about 1.5 inches.

6. The tampon of claim 4, wherein said at least one interval has a length that is in the range about 0.1 inch to about 1 inch.

7. The tampon of claim 4, wherein said at least one interval has a length that is in the range about 0.1 inch to about 0.5 inch.

8. The tampon of claim 4, wherein said at least one interval has a length that is in the range about 0.2 inch to about 0.5 inch.

9. The tampon of claim 4, wherein said at least one interval has a length that is about 0.25 inch.

10. The tampon of claim 1, wherein said absorbent layer in each of said plurality of segments has a uniform shape.

11. The tampon of claim 1, wherein said absorbent layer has a shape selected from the group consisting of circular, square, ovoid, hexagonal, rectangular, parallelogram, polygonal, and any combinations thereof.

12. The tampon of claim 10, wherein said uniform shape is selected from the group consisting of circular, square, ovoid, hexagonal, rectangular, parallelogram, polygonal, and any combinations thereof.

13. The tampon of claim 12, wherein said absorbent layer in each of said plurality of segments has a surface area that is in the range about 0.8 $in^2$ to about 6.0 $in^2$.

14. The tampon of claim 13, wherein said surface area of said absorbent layer of a first one of said plurality of segments differs from the surface area of said absorbent layer of a second one of said plurality of segments.

15. The tampon of claim 13, wherein said surface area of said absorbent layer in each of said plurality of segments is substantially the same.

16. The tampon of claim 12, wherein each of said plurality of segments has a plurality of absorbent layers positioned adjacent one another in a stack, and wherein said layer of semipermeable material in each of said plurality of segments is located at a first end of said stack.

17. The tampon of claim 16, wherein said layer of semipermeable material in one of said plurality of segments faces a withdrawal end of the tampon, and wherein said layer of semipermeable material of the remaining segments faces an adjacent one of said plurality of segments.

18. The tampon of claim 17, wherein said withdrawal end of said stack has a final segment that does not include said layer of semipermeable material.

19. The tampon of claim 17, wherein said withdrawal end of said stack has a final segment that has said layer of semipermeable material extended to surround said plurality of segments and form a cover.

20. The tampon of claim 19, wherein said cover is open at an insertion end of said stack of said plurality of segments.

21. The tampon of claim 19, wherein said cover completely encases said stack of said plurality of segments.

22. The tampon of claim 17, wherein said stack has an insertion end with a first segment that is attached to a withdrawal cord.

23. The tampon of claim 22, wherein said plurality of segments other than said first segment are not fixed to a point on said withdrawal cord allowing said remainder of said plurality of segments to float a distance along said cord.

24. The tampon of claim 23, wherein said distance is about 0.5 inches in either an insertion end direction or a withdrawal end direction along said withdrawal cord.

25. The tampon of claim 12, wherein said absorbent layer in each of said plurality of segments has a weight that is in the range about 0.1 grams to about 1.5 grams.

26. The tampon of claim 25, wherein said absorbent layer in each of said plurality of segments has a surface area about 2.67 $in^2$ and a weight about 0.4 grams.

27. A tampon comprising:
a coverstock bag, a withdrawal cord attached to said coverstock bag, and a plurality of segments positioned in said coverstock bag, each of said plurality of segments having at least one absorbent layer and at least one layer of semipermeable material, and
wherein said at least one layer of semipermeable material acts as an absorption barrier that restricts and delays substantial fluid absorption by the absorbent layer of a next one of said plurality of segments until said at least one absorbent layer of a preceding one of said plurality of segments has substantially absorbed and expanded.

28. The tampon of claim 27, wherein at least one of said plurality of segments includes two or more adjacent absorbent layers.

29. The tampon of claim 28, wherein each of said plurality of segments includes two or more adjacent absorbent layers.

30. The tampon of claim 27, wherein said at least one absorbent layer in said plurality of segment has a uniform shape.

31. The tampon of claim 30, wherein said uniform shape is selected from the group consisting of circular, square, ovoid, hexagonal, rectangular, parallelogram, polygonal, and any combinations thereof.

32. The tampon of claim 27, wherein said at least one absorbent layer has a surface area that is in the range about 0.8 $in^2$ to about 6.0 $in^2$.

33. The tampon of claim 32, wherein said surface area of said at least one absorbent layer of a first one of said plurality of segments differs from the surface area of said at least one absorbent layer of a second one of said plurality of segments.

34. The tampon of claim 32, wherein said surface area of said at least one absorbent layer of each of said plurality of segments is substantially the same.

35. The tampon of claim 27, wherein each of said plurality of segments has a plurality of said absorbent layers positioned adjacent one another in a stack, and wherein said at least one layer of semipermeable material in each of said plurality of segments is located at a first end of said stack.

36. The tampon of claim 35, wherein said at least one layer of semipermeable material of one of said plurality of segments faces a withdrawal end of said tampon, and wherein said at least one layer of semipermeable material of the remaining segments faces an adjacent one of said plurality of segments.

* * * * *